United States Patent
Kamohara et al.

(10) Patent No.: US 6,319,965 B1
(45) Date of Patent: Nov. 20, 2001

(54) MARGINAL TREATMENT MATERIAL OF DENTURE BASE AND MARGINAL TREATMENT METHOD

(75) Inventors: Hiroshi Kamohara; Makiko Takeo, both of Tokyo (JP)

(73) Assignee: GC Corporation, Tokyo (JP)

( * ) Notice: Subject to any disclaimer, the term of this patent is extended or adjusted under 35 U.S.C. 154(b) by 0 days.

(21) Appl. No.: 09/379,575

(22) Filed: Aug. 24, 1999

(30) Foreign Application Priority Data

Sep. 7, 1998 (JP) .................................................. 10-252414

(51) Int. Cl.$^7$ ............................. A61K 6/083; A61C 13/02
(52) U.S. Cl. ........................ 523/120; 523/118; 524/120; 524/493; 524/588; 524/731; 524/789; 524/862; 528/32; 438/199.1
(58) Field of Search ..................................... 523/118, 120; 524/493, 588, 731, 789, 862; 528/32; 433/199.1

(56) References Cited

U.S. PATENT DOCUMENTS

| 3,950,300 | * | 4/1976 | Hittmair et al. . |
| 4,550,030 | | 10/1985 | Ohi et al. . |
| 4,604,142 | | 8/1986 | Kamohara et al. . |
| 4,814,011 | | 3/1989 | Kamohara et al. . |
| 4,909,847 | | 3/1990 | Ohi et al. . |
| 4,911,759 | | 3/1990 | Ohi et al. . |
| 5,203,914 | | 4/1993 | Futami et al. . |
| 5,631,320 | | 5/1997 | Kamohara et al. . |
| 5,637,628 | | 6/1997 | Kamohara et al. . |
| 5,907,002 | | 5/1999 | Kamohara et al. . |
| 5,952,400 | * | 9/1999 | Hosoi et al. . |

* cited by examiner

Primary Examiner—Peter Szekely
(74) Attorney, Agent, or Firm—Oblon, Spivak, McClelland, Maier & Neustadt, P.C.

(57) ABSTRACT

A marginal treatment material of a denture base, comprising (A) 100 parts by weight of an organopolysiloxane having at least two aliphatic unsaturated hydrocarbons in one molecule and having a viscosity of 500~5,000 cs at 25° C.; (B) 0.5~30 parts by weight of an organohydrogen polysiloxane having at least three hydrogen atoms directly bonded to a silicon atom in one molecule; (C) 10~500 ppm, based on the total of the components (A) and (B), of a silicone-soluble platinum compound; and (D) 0.5~20 parts by weight of fine silica powder having a BET specific surface area of 50~500 m$^2$/g, whose surface is made hydrophobic. A marginal treatment method of a denture base is also disclosed, comprising applying the marginal treatment material of the denture base to a marginal portion of a denture base lined by a soft lining material, followed by curing, and by applying the marginal treatment material to a border line between the denture base in the denture marginal portion and the soft lining material, followed by curing, can be easily form without polishing a smooth transitional surface.

2 Claims, 1 Drawing Sheet

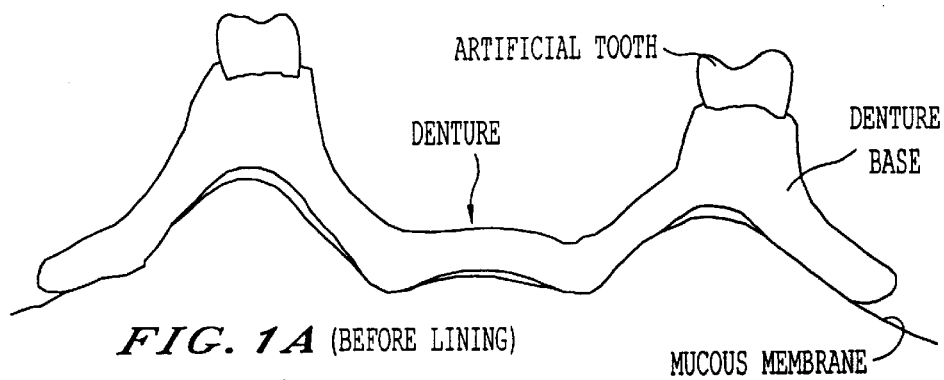
FIG. 1A (BEFORE LINING)
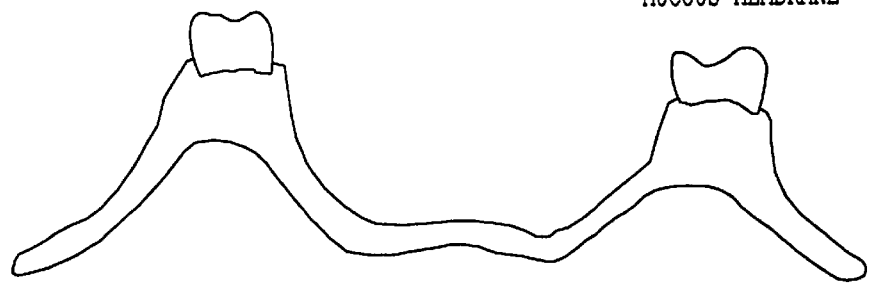
FIG. 1B (AFTER GRINDING)
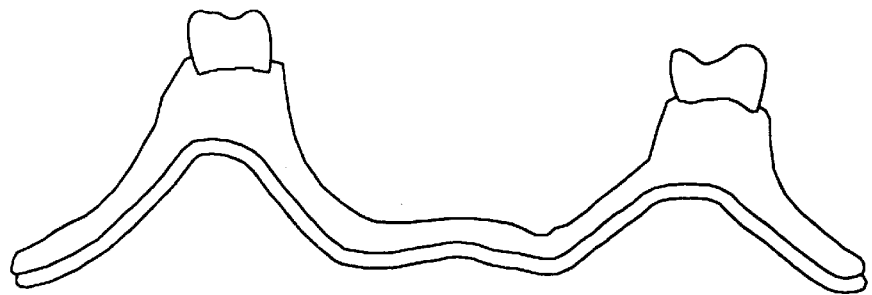
FIG. 1C (AFTER LINING)
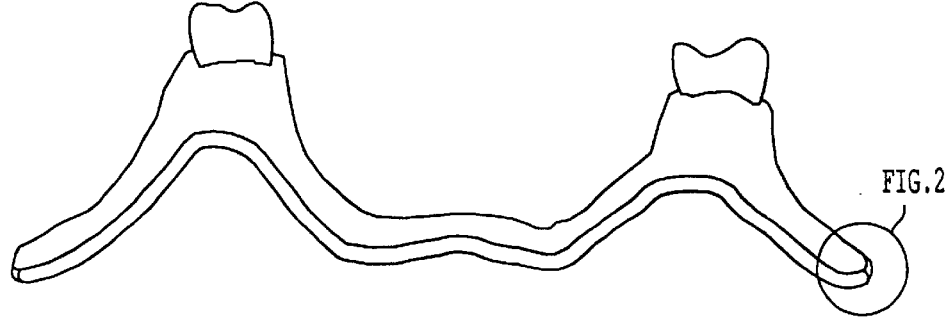
FIG. 1D (AFTER MARGINAL TREATMENT)
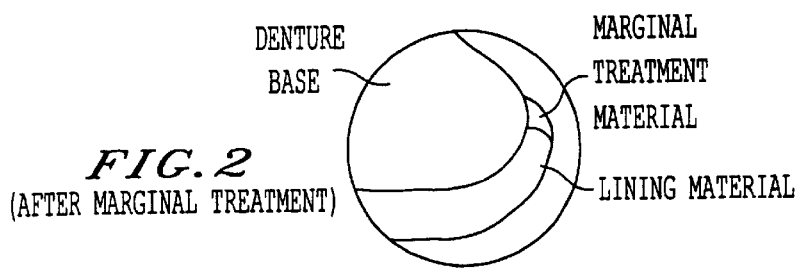
FIG. 2 (AFTER MARGINAL TREATMENT)

MARGINAL TREATMENT MATERIAL OF DENTURE BASE AND MARGINAL TREATMENT METHOD

BACKGROUND OF THE INVENTION

1. Field of the Invention

The present invention relates to a novel marginal treatment material which is used in a marginal portion of a denture base lined by a soft lining material and to a marginal treatment method of a denture base using this marginal treatment material.

2. Description of the Related Art

Of patients who set a denture, there has been patients whose mucous membranes become thin. Such patients suffer a strong contact between a denture base and a mucous membrane generating to cause a pain. In order to mitigate this pain, a lining method in which a silicone rubber is adhered to a surface of the denture base to be faced at the mucous membrane side is employed. Materials which are used for this lining method are generally called a soft lining material, and a heat-curing type silicone and a room temperature-curing type silicone are used. In recent years, the room temperature-curing type silicone has been widely used because its operation is simple. The lining using such a soft lining material is carried out by applying and building up the soft lining material on the surface of the denture base to be faced at the mucous membrane side, fitting and adjusting the resulting lining material on a cast in an oral cavity or in a flask (or an articulator), and then curing and adhering it. During this time, a border line between the denture base in the denture marginal portion and the soft lining material is polished by a polishing material, thereby finishing it to form a smooth transitional surface.

However, since this soft lining material is of a rubber, not only it is difficult to be polished, but also several kinds of polishing materials must be used until polishing completes. Accordingly, it took a long period of time to accomplish the polishing work. Also, since this polishing work is concerned with the polishing of the border line between the denture base and the soft lining material, there was a high risk that the soft lining material peels apart from the denture base or the soft lining material is torn off. In addition, since even after the finishing, the polished surface is rougher than a polished surface of a usual denture base, a rub between the polished surface and the mucous membrane in the oral cavity of a patient is generated. As a result, the patient was likely given a strong feeling of foreign matter and even a pain to the patient. As described above, in polishing the border line between the denture base in the denture marginal portion and the soft lining material, thereby finishing it to form a smooth transitional surface were involved various problems. Under such circumstances, the development of a marginal treatment material and a marginal treatment method without polishing was demanded.

BRIEF DESCRIPTION OF THE DRAWING

FIGS. 1A–1D and 2 illustrate sectional views of a denture and a mucous membrane before lining, after grinding, after lining, and after marginal treatment.

SUMMARY OF THE INVENTION

Thus, an object of this invention is to develop a marginal treatment material of a denture base capable of forming a smooth transitional surface on a border line between a denture base in a denture marginal portion and a soft lining material without polishing as well as a marginal treatment method using this marginal treatment material. Another object of the invention is to carry out the marginal treatment method easily within a short period of time.

In order to achieve the above-described objects, the present inventors made extensive and intensive investigations. As a result, it has been found that when a marginal treatment material of a denture base comprising a silicone rubber having high fluidity and a proper transparency is applied to a border line between the denture base in the denture marginal portion and the soft lining material and then cured, a smooth transitional surface can be easily formed without polishing, leading to the accomplishment of the invention.

That is, this invention provides a marginal treatment material of a denture base comprising:

(A) 100 parts by weight of an organopolysiloxane having at least two aliphatic unsaturated hydrocarbons in one molecule and having a viscosity of 500~5,000 cs at 25° C.;

(B) 0.5~30 parts by weight of an organohydrogen polysiloxane having at least three hydrogen atoms directly bonded to a silicon atom in one molecule;

(C) 10~500 ppm, based on the total of the components (A) and (B), of a silicone-soluble platinum compound; and (D) 0.5~20 parts by weight of fine silica powder having a BET specific surface area of from 50 to 500 $m^2/g$, whose surface is made hydrophobic.

Also, the invention provides a marginal treatment method of a denture base comprising applying this marginal treatment material to a marginal portion of a denture base line with a soft lining material and then curing it.

DETAILED DESCRIPTION OF THE INVENTION

FIGS. 1A–1D and 2 explain the meaning of marginal treatment of a denture base.

The marginal treatment material of the denture base comprising the foregoing components (A) to (D) according to the present invention well flows in a margin of the soft lining material and has good adhesion to the denture base. For these reasons, a border line between the soft lining material and the denture base can be finished to form a smooth transitional surface. Since the thus finished border line has a proper transparency, it becomes a coating film fitted to the shades of both of the soft lining material and the denture base. As a result, the border line can be visually seen as a smooth transitional surface, and a patient does not feel physical disorder.

The component (A) of the marginal treatment material of the denture base according to the present invention is an organopolysiloxane having at least two aliphatic unsaturated hydrocarbons in one molecule and having a viscosity of 500~5,000 cs at 25° C. This organopolysiloxane is preferably a linear one, the both terminals of its molecular chain being hindered by a vinylsilyl group. This terminal vinyl group may be plural, or the vinyl group may be contained in the chain. when the viscosity of the organopolysiloxane is less than 500 cs at 25° C., the margin is liable to peel apart because a tear strength of the cured material is lowered. On the other hand, when it exceeds 5,000 cs at 25° C., the application becomes difficult. Accordingly, the both cases are not suitable.

The component (B), organohydrogen polysiloxane, of the marginal treatment material of the denture base according to the present invention must have at least three hydrogen atoms directly bonded to a silicon atom in one molecule. Since this compound functions as a crosslinking agent, its content greatly influences the curing characteristics. When the amount of the organohydrogen polysiloxane is less than 0.5 parts by weight based on 100 parts by weight of the component (A), not only the curing speed becomes slow, but also the surface of the cured material becomes sticky. As a result, the shape of the margin after the marginal treatment is liable to deform. On the other hand, when it exceeds 30 parts by weight, the operation time for carrying out the marginal treatment is extremely short, so that the marginal treatment is not sufficiently carried out.

As the component (C), silicone-soluble platinum compound, of the marginal treatment material of the denture base according to the present invention are useful known addition reaction catalysts such as chloroplatinate, alcohol-modified chloroplatinates, a complex of chloroplatinate with olefins, and the like. A chloroplatinate-vinylsiloxane complex is especially preferable. An amount of the component (C) to be added is in a range of 10~500 ppm based on the total of the components (A) and (B). When it is less than 10 ppm, there are disadvantages that the curing speed is slow and that even in case where a trace amount of a substance inhibiting the catalytic ability is present, the curing is delayed. On the other hand, when it exceeds 500 ppm, the curing is too fast, and the cured material becomes yellow with a lapse of time as well, whereby the shade of the margin is liable to change. It is preferred that the silicone-soluble platinum compound such as chloroplatinate is dissolved in an alcoholic, ketone-based, ether-based, or hydrocarbon-based solvent, a polysiloxane oil, or the like and then used.

The component (D), fine silica powder, of the marginal treatment material of the denture base according to the present invention is fine silica powder having a BET specific surface area of 50~500 m$^2$/g, whose surface is made hydrophobic. This hydrophobic fine silica powder is obtained by heat treatment of hydrophilic silica, for example, fumed silica with a surface treatment agent such as methyl trichlorosilane, dimethyl dichlorosilane, trimethyl chlorosilane, or corresponding alkoxysilanes, octamethyl cyclotetrasiloxane, hexamethyl disiloxane, hexamethyl disilazane, or mixtures thereof, or a combination of this surface treatment agent and water. As the hydrophobic silica, ones in which the whole or a major part of the active silanol groups present on the surface thereof are hindered by a hydrophobic group of a $(CH_3)_3SiO_{1/2}$, $(CH_3)_2SiO_{2/2}$ or $CH_3SiO_{3/2}$ unit are useful. This hydrophobic fine silica powder has an effect for increasing the tear strength while properly keeping the transparency of the cured material as the marginal treatment material. Also, it has effects for improving the lapsing stability of the shade of the cured material and for keeping the shade fitness of the marginal treatment material to the denture base or the soft lining material in the oral cavity over a long period of time. This hydrophobic silica must have a BET specific surface area of 50~500 m$^2$/g. When the BET specific surface area is less than 50 m$^2$/g, the cured material is opaque, and the tear strength is not satisfactory, and hence, such is not suitable. On the other hand, when it exceeds 500 m$^2$/g, the viscosity is excessively high, so that the application operation becomes difficult. Accordingly, such being not proper. An amount of the hydrophobic fine silica powder to be compounded is in a range from 0.5 to 20 parts by weight based on 100 parts by weight of the component (A). When the amount of the component (D) to be compounded is less than 0.5 parts by weight, the tear strength of the cured material is not satisfactory, so that after the marginal treatment, the breakage likely occurs after setting in the oral cavity. On the other hand, when it exceeds 20 parts by weight, the application operation is extremely difficult, so that the marginal treatment can not be sufficiently carried out.

In carrying out the marginal treatment using the marginal treatment material of the denture base comprising the components (A) to (D), the denture base is first lined by a soft lining material in the customary manner, and the state of the marginal portion is examined. In case where an excessive area is generated in the marginal portion, the excessive area is cut off by means of a knife or the like. Next, the above-described marginal treatment material of the denture base which is a liquid is applied to a border line between the soft lining material and the denture base by using a sponge, a brush, or the like, and after curing, the denture base is returned into the oral cavity of a patient, whereby a fitting feeling, etc. of the patient are confirmed. The marginal treatment of the denture base is thus completed by this simple operation. In the marginal treatment on the border line between the marginal portion of the denture base and the soft lining material by the marginal treatment material of the denture base according to the present invention, the polishing operation which has hitherto been carried out is not required at all. Also, the shade of the margin can be finished so as to be in good harmony with the denture base or the soft lining material.

In the marginal treatment material of the denture base according to the present invention, so far as the characteristics are not lost, various inorganic or organic coloring agents such as red oxide and fused azo pigments can be used. However, these coloring agents must be used within a range where the shade fitness between the denture base and the soft lining material is not lost. In addition, in the marginal treatment method, an adhesive and the like may be used, if desired.

The present invention is hereunder described in more detail with reference to the following Examples, but it should not be construed that the invention is limited thereto.

EXAMPLE 1

A base paste and a catalyst paste, each having the following composition, were prepared.

| (Base paste) | |
|---|---|
| Dimethyl polysiloxane having a viscosity of 2,000 cs at 25° C., the both terminals of its molecular chain being hindered by a methyl vinylsiloxy group: | 100 parts by weight |
| Linear methyl hydrogen polysiloxane containing 20% by mole of a methyl hydrogen siloxane unit: | 10 parts by weight |
| Hydrophobic fine silica powder having a BET specific surface area of 50 m$^2$/g, the surface of which is hindered by a $(CH_3)_3SiO_{1/2}$ unit: | 5 parts by weight |
| (Catalyst paste) | |
| Dimethyl polysiloxane having a viscosity of 2,000 cs at 25° C., the both terminals of its molecular chain being hindered by a dimethyl vinylsiloxy group: | 100 parts by weight |

| -continued | |
|---|---|
| Silicone oil solution containing 0.3% by weight of a 1,3-divinyl tetra-methyldisiloxane-platinum complex: | 5 parts by weight |
| Hydrophobic fine silica powder having a BET specific surface area of 500 m$^2$/g, the surface of which is hindered by a (CH$_3$)$_3$SiO$_{1/2}$ unit: | 5 parts by weight |

First of all, in order to confirm whether or not a marginal treatment material of a denture base having the above-described composition had a sufficient strength, a tear strength of a cured material was measured. The test of the tear strength was carried out in accordance with JIS K6301 after weighing equal amounts of the base paste and the catalyst paste. The results obtained are shown in Table 1. Next, according to the customary manner, after lining the denture base by a soft lining material (a trade name: GC Denture Relining, made by GC Corporation), equal amounts of the base paste and the catalyst paste were kneaded, and the mixture was applied to a marginal portion of the soft filing material by means of a sponge, followed by curing. Thereafter, the resulting denture was returned into the oral cavity of the patient. One month later, the marginal state was observed in terms of the shade and the state of peeling. Also, the state of the patient was evaluated in terms of the condition after the patient had been set the denture for one month. Further, the time required for the marginal treatment is also shown in Table 1.

As shown in Table 1, the time required for the marginal treatment was one-half or less than that in Comparative Example 1 as described later, wherein the marginal treatment by polishing was carried out, and no peeling of the margin was observed. Also, the setting feeling of the patient was good. On the other hand, in the denture of the patient, wherein the marginal treatment by polishing was carried out, peeling on the margin of the soft lining material was partly observed, and following this, the patient complained of a pain. In Comparative Example 2 as also described later, wherein the marginal treatment was carried out in the same manner as in Example 1, except that the hydrophobic fine silica powder was not used, the tear strength of the resulting cured material was markedly lowered. Though the time required for the marginal treatment was short as in the respective Examples, after the patient-had set the denture, a part of the cured material was broken, and the shade became somewhat yellow.

EXAMPLE 2

A base paste and a catalyst paste, each having the following composition, were prepared.

| (Base paste) | |
|---|---|
| Dimethyl polysiloxane having a viscosity of 5,000 cs at 25° C., the both terminals of its molecular chain being hindered by a methyl vinylsiloxy group: | 100 parts by weight |
| Linear methyl hydrogen polysiloxane containing 20% by mole of a methyl hydrogen siloxane unit: | 60 parts by weight |

| -continued | |
|---|---|
| Hydrophobic fine silica powder having a BET specific surface area of 50 m$^2$/g, the surface of which is hindered by a (CH$_3$)$_3$SiO$_{1/2}$ unit: | 1 part by weight |
| (Catalyst paste) | |
| Dimethyl polysiloxane having a viscosity of 5,000 cs at 25° C., the both terminals of its molecular chain being hindered by a dimethyl vinylsiloxy group: | 100 parts by weight |
| Silicone oil solution containing 0.3% by weight of a 1,3-divinyl tetra-methyldisiloxane-platinum complex: | 5 parts by weight |
| Hydrophobic fine silica powder having a BET specific surface area of 500 m$^2$/g, the surface of which is hindered by a (CH$_3$)$_3$SiO$_{1/2}$ unit: | 1 part by weight |

The same tests as in Example 1 were carried out, and the results are shown in Table 1. The results obtained in this Example were good as in Example 1. The time required for the marginal treatment was markedly short as compared with that in Comparative Example 1 wherein the marginal treatment by polishing was carried out. No changes in the peeling and the shade were observed. Also, the setting feeling of the patient was good.

EXAMPLE 3

A base paste and a catalyst paste, each having the following composition, were prepared.

| (Base paste) | |
|---|---|
| Dimethyl polysiloxane having a viscosity of 500 cs at 25° C., the both terminals of its molecular chain being hindered by a methyl vinylsiloxy group: | 100 parts by weight |
| Linear methyl hydrogen polysiloxane containing 20% by mole of a methyl hydrogen siloxane unit: | 1 part by weight |
| Hydrophobic fine silica powder having a BET specific surface area of 500 m$^2$/g, the surface of which is hindered by a (CH$_3$)$_3$SiO$_{1/2}$ unit: | 20 parts by weight |
| (Catalyst paste) | |
| Dimethyl polysiloxane having a viscosity of 500 cs at 25° C., the both terminals of its molecular chain being hindered by a dimethyl vinylsiloxy group: | 100 parts by weight |
| Silicone oil solution containing 0.3% by weight of a 1,3-divinyl tetra-methyldisiloxane-platinum complex: | 3 parts by weight |
| Hydrophobic fine silica powder having a BET specific surface area of 500 m$^2$/g, the surface of which is hindered by a (CH$_3$)$_3$SiO$_{1/2}$ unit: | 20 parts by weight |

The same tests as in Example 1 were carried out, and the results are shown in Table 1. The results obtained in this Example were good as in Example 1. The time required for the marginal treatment was markedly short as compared with that in Comparative Example 1 wherein the marginal treatment by polishing was carried out. No changes in the peeling and the shade were observed. Also, the setting feeling of the patient was good.

COMPARETIVE EXAMPLE 1

According to the customary manner, a denture base was lined by the soft lining material in the same manner as in Example 1. Then, the margin was treated by polishing. The polishing was carried out by using a silicone point. Thereafter, the resulting denture was returned into the oral cavity of the patient. One month later, the marginal state and the setting feeling of the patient were examined. The results are shown in Table 1.

COMPARATIVE EXAMPLE 2

A base paste and a catalyst paste, each having the following composition, were prepared.

| (Base paste) | |
|---|---|
| Dimethyl polysiloxane having a viscosity of 5,000 cs at 25° C., the both terminals of its molecular chain being hindered by a methyl vinylsiloxy group: | 100 parts by weight |
| Linear methyl hydrogen polysiloxane containing 20% by mole of a methyl hydrogen siloxane unit: | 10 parts by weight |
| (Catalyst paste) | |
| Dimethyl polysiloxane having a viscosity of 500 cs at 25° C., the both terminals of its molecular chain being hindered by a dimethyl vinylsiloxy group: | 100 parts by weight |
| Silicone oil solution containing 0.3% by weight of a 1,3-divinyl tetra-methyldisiloxane-platinum complex: | 5 parts by weight |

The same tests as in Example 1 were carried out, and the results are shown in Table 1. The tear strength of the resulting cured material was markedly lowered. Though the time required for the marginal treatment was short as in the respective Examples, after the patient had set the denture, a part of the cured material was broken, and the shade became somewhat yellow.

treatment can be carried out within a short period of time neither causing peeling of the margin and discoloration nor generating a pain of a mucous membrane to a patient to be caused by the peeling of the margin, through a simple treatment in which the marginal treatment material is applied to a border line between the denture base and the soft lining material and then cured, without carrying out the polishing as in the conventional art. In particular, the present invention is largely effective for overcoming the disorder in lining by a soft lining material which has hitherto been applied to patients of a serious disease and hence, it should greatly contribute in the dental field.

While the present invention has been described in detail and with reference to specific embodiments thereof, it will be apparent to one skilled in the art that various changes and modifications can be made therein without departing from the sprit and scope thereof.

What is claimed is:

1. A marginal treatment material of a denture base, Consisting essentially of:
   (A) 100 parts by weight of an organopolysiloxane having at least two aliphatic unsaturated hydrocarbons in one molecule and having a viscosity of from 500 to 5,000 cs at 25° C.;
   (B) 0.5~30 parts by weight of an organohydrogen polysiloxane having at least three hydrogen atoms directly bonded to a silicon atom in one molecule;
   (C) 10~500 ppm, based on the total of the components (A) and (B), of a silicone-soluble platinum compound; and
   (D) 0.5~20 parts by weight of fine silica powder having a BET specific surface area of from 50 to 500 $m^2/g$, whose surface is made hydrophobic.

2. A marginal treatment method of a denture base, which comprises applying a marginal treatment material of a denture base, comprising:
   (A) 100 parts by weight of an organopolysiloxane having at least two aliphatic unsaturated hydrocarbons in one molecule and having a viscosity of 500~5,000 cs at 25° C.;

TABLE 1

| | Example | | | Comparative Example | |
|---|---|---|---|---|---|
| | 1 | 2 | 3 | 1 | 2 |
| Tear strength (kg/cm) | 5.6 | 5.2 | 4.8 | — | 1.2 |
| Time required for the marginal treatment | About 3 minutes | About 3 minutes | About 3 minutes | About 7 minutes | About 3 minutes |
| Marginal state | Neither peeling nor discoloration was observed. | Neither peeling nor discoloration was observed. | Neither peeling nor discoloration was observed. | Peeling was observed in a part of the soft lining material. | Peeling was observed in the margin, and yellowing was somewhat observed. |
| Condition of patient | Good | Good | Good | The patient complained of a pain. | The patient complained of a pain. |

It has been confirmed from the results shown in Table 1 that the marginal treatment material of the denture base according to the present invention has a high tear strength, does not cause peeling or discoloration, and is good in the marginal state; it is good in the fitness in the oral cavity of a patient; and that since the time required for the marginal treatment is one-half less than that in the related art marginal treatment by polishing, the marginal treatment can be easily carried out.

In the light of the above, when the marginal treatment material and the marginal treatment method according to the present invention are employed, in the marginal treatment of a denture base lined by a soft lining material, the marginal (B) 0.5~30 parts by weight of an organohydrogen polysiloxane having at least three hydrogen atoms directly bonded to a silicon atom in one molecule;
   (C) 10~500 ppm, based on the total of the components (A) and (B), of a silicone-soluble platinum compound; and
   (D) 0.5~20 parts by weight of fine silica powder having a BET specific surface area of from 50 to 500 $m^2/g$, whose surface is made hydrophobic, to a marginal portion of a denture base lined by a soft lining material, followed by curing.

* * * * *